(12) United States Patent
Dupont et al.

(10) Patent No.: US 6,452,035 B2
(45) Date of Patent: Sep. 17, 2002

(54) SULFATION PROCESS

(75) Inventors: Jeffrey Scott Dupont; Eugene Paul Gosselink, both of Cincinnati, OH (US)

(73) Assignee: The Procter & Gamble Co., Cincinnati, OH (US)

( * ) Notice: Subject to any disclaimer, the term of this patent is extended or adjusted under 35 U.S.C. 154(b) by 0 days.

(21) Appl. No.: 09/920,032

(22) Filed: Aug. 1, 2001

Related U.S. Application Data

(60) Provisional application No. 60/223,301, filed on Aug. 7, 2000.

(51) Int. Cl.⁷ .................... C07C 305/00; C07C 315/00
(52) U.S. Cl. ............................. 558/20; 568/27
(58) Field of Search ................ 558/20; 568/27

(56) References Cited

U.S. PATENT DOCUMENTS

| | | | | |
|---|---|---|---|---|
| 5,037,992 A | * | 8/1991 | Ward et al. ............... | 558/36 |
| 6,235,913 B1 | * | 5/2001 | Raths et al. ............... | 554/98 |
| 6,346,509 B1 | * | 2/2002 | Kadono et al. ............ | 510/535 |

FOREIGN PATENT DOCUMENTS

DE    25 57 791 A1    12/1975

* cited by examiner

Primary Examiner—Deborah C. Lambkin
(74) Attorney, Agent, or Firm—Richard S. Echler, Sr.; C. Brant Cook; Kim William Zerby

(57) ABSTRACT

The present invention relates to a sulfation process comprising the steps of:

a) reacting a tertiary amine with a sulfation precursor having the formula:

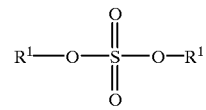

wherein $R^1$ is $C_1$–$C_{22}$ alkyl, $C_7$–$C_{22}$ alkylenearyl, and mixtures thereof; to form an admixture comprising a quaternized amine and a sulfating species; and b) reacting a hydroxyl species with said admixture to form a sulfated hydroxyl species.

The process of the present invention is adaptable to sulfating a wide range of alcohols including the hydroxyl unit which terminates a polyalkoxylate moiety which are prevalent in the area of surfactants, inter alia, alkyl ethoxy sulfates.

34 Claims, No Drawings

SULFATION PROCESS

This Application claims priority to United States Provisional Patent Application Serial No. 60/223,301 filed Aug. 7, 2000.

FIELD OF THE INVENTION

The present invention relates to a convenient, high yield process for sulfating alcohols. The process of the present invention is adaptable to sulfating a wide range of alcohols including the hydroxyl unit which terminates a polyalkoxylate moiety which are prevalent in the area of surfactants, inter alia, alkyl ethoxy sulfates. The sulfation process of the present invention can be used to sulfate poly-alcohols or amino alcohols, the latter which can serve to provide a key element necessary for sulfation.

BACKGROUND OF THE INVENTION

The most common process for manufacturing alcohol sulfates encompasses falling film reaction techniques. This process most often uses $SO_3$ as the sulfation reagent to sulfate the parent alcohol. While this technique is well known in the industry, it requires specialized equipment and can produce unwanted side products. In particular, dioxane is usually produced by side reactions when ethoxylated materials are involved. Other complications in falling film sulfation can lead to salt by-products, over-sulfation and color/odor issues. In addition, falling film reactors are not easily adapted for use in sulfating alcohols wherein the desired product is a non-aqueous, high active composition due to the industry practice of using aqueous base such as sodium hydroxide to neutralize the acidic initial sulfation product.

There is therefore a long felt need to provide a convenient process for controllably sulfating hydroxy units without the need for specialized equipment. There is also a long felt need for a process for sulfating alcohols to produce a non-aqueous, high active product. In addition, there is a long felt need for a alcohol sulfation process which minimizes unwanted side reactions and salts. In addition, there is a long felt need to controllably sulfate amino alcohols, the product of which process yields zwitterionic materials, for example, surfactants.

SUMMARY OF THE INVENTION

The present invention meets the aforementioned needs in that it has been surprisingly discovered that hydroxyl moieties can be controllably sulfated by the trans-sulfation process described herein. In an important embodiment of the present invention, a portion of the substrate to be sulfated, can serve as a reagent participating in the process as an essential element or component, for example, as a source of amino moiety. The sulfation process of the present invention allows the formulator to introduce into the molecule to be sulfated a pre-determined degree of sulfation. In addition, the reagents which are required to perform the process of the present invention minimize unwanted by-products, inter alia, inorganic salt by-products due to neutralization, or side products, inter alia, dioxane and other cyclic ethers. The process of the present invention can be conducted in standard chemical reaction vessels instead of specialized equipment such as falling film reactors. A further advantage of the present process is the ability to produce anhydrous, high active sulfated alcohols.

The first object of the present invention relates to a sulfation process comprising the steps of:

a) reacting a tertiary amine with a sulfation precursor having the formula:

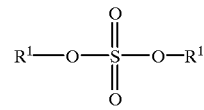

wherein $R^1$ is $C_1$–$C_{22}$ alkyl, $C_7$–$C_{22}$ alkylenearyl, and mixtures thereof; to form an admixture comprising a quaternized amine and a sulfating species; and b) reacting a hydroxyl species with said admixture to form a sulfated hydroxyl species.

A further aspect of the present invention relates to a trans-sulfation process comprising the steps of:

a) reacting n equivalents of an amine moiety with n equivalents of a sulfation precursor to form n equivalents of a sulfating species; and b) reacting said n equivalents of a sulfating species with a substrate having n hydroxyl moieties to form a compound having n sulfated hydroxyl moieties.

The present invention also relates to a trans-sulfation process comprising the steps of:

a) reacting n equivalents of a tertiary amine moiety with n equivalents of a sulfation precursor to form n equivalents of a sulfating species; and b) reacting said n equivalents of a sulfating species with a substrate having m equivalents of hydroxyl moieties to form a compound having up to n sulfated hydroxyl moieties.

A yet further aspect of the present invention relates to a trans-sulfation process comprising the steps of:

a) reacting an amine-comprising compound having n equivalents of amine moieties and an auxiliary amine having n' equivalents of amine moieties with n+n' equivalents of a sulfation precursor to form n+n' equivalents of sulfating species, and wherein said amine-comprising compound further comprises m hydroxyl moieties; and b) forming m or less sulfated hydroxyl moieties.

These and other objects, features and advantages will become apparent to those of ordinary skill in the art from a reading of the following detailed description and the appended claims. All percentages, ratios and proportions herein are by weight, unless otherwise specified. All temperatures are in degrees Celsius (°C.) unless otherwise specified. All documents cited are in relevant part, incorporated herein by reference.

DETAILED DESCRIPTION OF THE INVENTION

The present invention relates to a process for sulfating hydroxyl moieties. The process of the present invention in the most general view is a trans-sulfation process comprising a step which forms a sulfating species and a step which provides controllable sulfation of one or more hydroxyl moieties.

Importantly, the process of the present invention can be used to selectively and controllably sulfate the hydroxyl moieties which terminate alkoxylated or polyalkoxylated units, inter alia, alcohols, polyols, saccharides, amines, and polyamines, including polyalkyleneimines. The process of the present invention is especially adaptable to compounds which comprise one or more tertiary nitrogens said nitrogens to be subsequently quaternized.

For the purposes of the present invention the term "hydroxyl-comprising compound" is defined herein as "any organic or inorganic compound having a hydroxyl moiety, —OH, which is capable of being sulfated by the process of the present invention." Preferably the "hydroxyl-comprising compound" is a compound which is the compound to be sulfated.

For the purposes of the present invention the term "amine-comprising compound" is defined herein as "any organic or inorganic compound having at least one un-oxidized nitrogen, for example, a nitrogen which is not an N-oxide nitrogen, which is capable of accepting an $R^1$ unit as defined herein below and thereby generating a sulfating species as described herein below."

For the purposes of the present invention the terms "sulfation precursor" and "sulfating species" are used interchangeably and are taken to mean a reagent as defined herein below which when reacted in step (a) of the present process forms a chemically reactive species, "sulfation species", which further reacts to sulfate hydroxyl moieties.

The first required step of the present process, Step (a), is conducted under non-acidic conditions. The second required step of the present process, Step (b), is conducted under acidic conditions.

The following describes the required steps of the present process.

Step (a): Formation of a "sulfating species". Formation of a sulfating species is the first required step of the process of the present invention.

In a preferred embodiment of the present invention, one equivalent of a sulfation precursor (sulfating agent) is reacted with one tertiary amine moiety to form one equivalent of a sulfating species. In a second embodiment of the present invention, one equivalent of a sulfation precursor is reacted with one amine moiety to form one equivalent of a sulfating species.

In another embodiment of the present invention, up to two equivalents of a sulfating agent is reacted with one secondary amine moiety to form, up to two equivalents of sulfating species. In yet another embodiment, up to three equivalents of sulfating agent is reacted with one primary amine moiety to form up to three equivalents of sulfating species. In the case where a non-tertiary amine is being alkylated multiple times, it is preferred to provide adequate basicity such that unprotonated amine sites remain available for the alkylation steps. The artisan will understand that when a non-tertiary amine moiety is being used, which can be alkylated multiple times with formation of multiple equivalents of sulfation species, the artisan may choose to conduct the process stepwise alternating the alkylation and sulfation steps to achieve the desired level of sulfation.

If desired the process of the present invention may be conducted in the presence of a solvent, preferably non-reactive solvents, inter alia, glyme, diglyme, are used.

In a preferred embodiment of the present invention, wherein a tertiary amine is employed to form the sulfation species, the products which are formed in Step (a) are one equivalent of a sulfating species and one equivalent of a quaternary ammonium compound, an example of which is depicted in the general scheme:

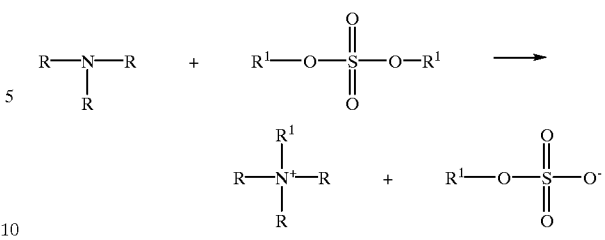

wherein the amine may (optionally comprise more than one tertiary amino moiety.

Non-limiting examples of tertiary amines include trimethyl amine, triethyl amine, tripropyl amine, tributyl amine, N-alkyl piperidine, N,N-dialkyl piperazine, N-alkyl morpholine, N-alkyl pyrrolidine, N,N,N',N'-tetraalkyl alkylenediamines, N-alkyl polyalkyleneamines, N-alkyl polyalkyleneimines, polyalkyleneimines, and mixtures thereof.

The preferred sulfation precursors according to the present invention have the formula:

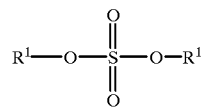

wherein $R^1$ is $C_1$–$C_{22}$ alkyl, $C_7$–$C_{22}$ alkylenearyl, and mixtures thereof; preferably $R^1$ is methyl, ethyl, propyl, butyl, benzyl, and mixtures thereof; more preferably methyl. In certain embodiments of the present invention, one $R^1$ is an alkylbenzyl moiety and the other is methyl.

A non-limiting example of Step (a) according to the present invention, is the formation of a sulfating species comprising the step of reacting one equivalent of a tertiary amine which includes the target hydroxyl to be sulfated with one equivalent of a sulfation precursor is represented by the scheme:

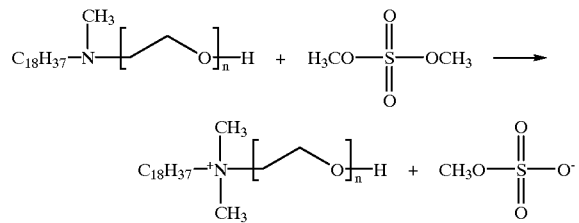

The following example of the formation of a sulfating species comprising the step of reacting one equivalent of a tertiary amine that does not include a sulfatable hydroxyl with one equivalent of a sulfation precursor is represented by the scheme:

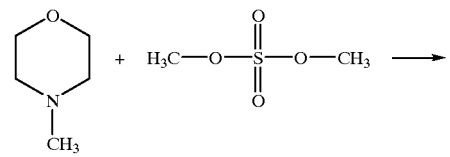

-continued

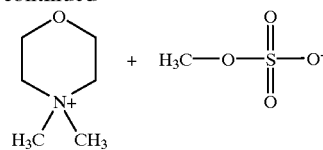

wherein N,N-dimethyl morpholine quaternary ammonium salt is formed and $CH_3OSO_3^-$ is the sulfating species.

The following is an example wherein the molecule which provides the source of tertiary amine comprises more than one tertiary amine moieties:

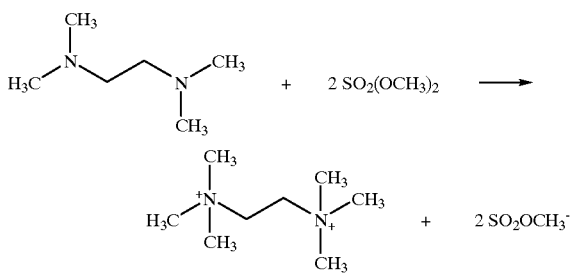

and wherein two equivalents of a sulfating species can be formed per molecule of tertiary amine-comprising compound employed.

In another embodiment of Step(a) of the present invention, a non-tertiary amine is reacted with a sulfation precursor to form an alkylated amine and a sulfating species according to the scheme:

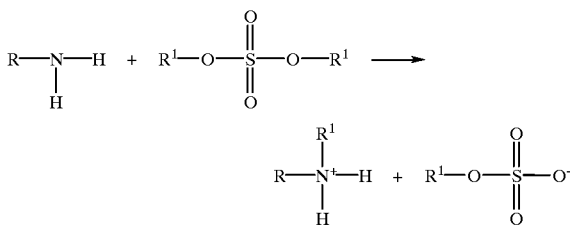

Step (a) of the process of the present invention is conducted under basic or non-acidic conditions at a temperature of from about 0° C. to about 200° C. The reaction when exothermic can be controlled by any suitable means, inter alia, cooling the reaction vessel, providing a reflux condenser.

When the hydroxyl moiety comprising compound which is to be sulfated also comprises an amine unit which the formulator does not wish to be affected during the trans-sulfation process, the formulator may add an auxiliary amine, preferably in excess of the stoichiometric amount required. Auxiliary amines may be used when the number of amine units in the hydroxyl moiety comprising compound has an insufficient number of amine moieties to successfully sulfate each hydroxyl moiety.

Step (b): Trans-sulfation step. The formation of a sulfated hydroxyl species is the second required step of the process of the present invention. One equivalent of a sulfating species is required per hydroxyl moiety which is to be sulfated. The products which are formed in Step (b) of the present invention can be depicted by the general scheme:

wherein said sulfated alcohol (hydroxyl moiety) can be isolated as a zwitterionic species especially when the alcohol to be sulfated serves as the source of nitrogen. The product of sulfation can be isolated as, the protonated species $ROSO_3H$, or a salt $ROSO_3M$. M can be any suitable salt forming cation, preferably, ammonium, lithium, sodium, potassium, magnesium, calcium, barium, and mixtures thereof; more preferably sodium or the ammonium cation which was the counter ion of the sulfating species.

Step (b), which must be conducted under acidic conditions, can employ any suitable acid, inter alia, sulfuric acid, hydrochloric acid, methanesulfonic acid, or Lewis acids, inter alia, boron trifluoride.

The acid catalyst can be added in any amount sufficient to form the desired product, however, the process of the present invention is conducted at a pH less than about 6, preferably less than about 4.5, more preferably less than about 3, most preferably Step (b) is conducted at a pH less than about 2. If fact, acid level of from about 0.01 molar to 1 molar are preferred.

The acid catalyst can be introduced by any manner which is convenient to the formulator, however, good mixing should be utilized. Alternatively, the acid may be generated in situ by adding excess sulfating agent and allowing this excess agent to react with a limited source of proton, inter alia, water. Unreacted alcohol units (under circumstances wherein not all —OH units are to be sulfated) can be carried over into Step (b) from Step (a).

Step (b) of the process of the present invention is conducted at a temperature of from about 0° C. to about 200° C. The reaction when exothermic can be controlled by any suitable means, inter alia, cooling the reaction vessel, providing a reflux condenser.

One aspect of Step (b) can be used by the formulator to help drive the reaction to completion or to control the level of sulfation. For example, as depicted in the following scheme wherein dimethyl sulfate is used in Step (a) as the sulfation precursor:

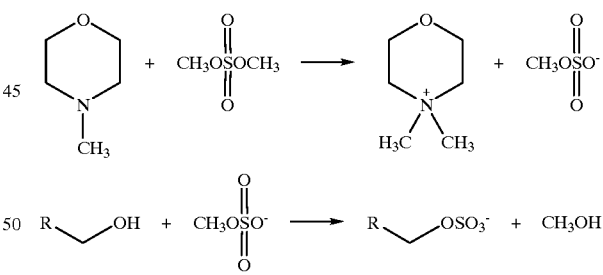

methanol is a by-product of the trans-sulfation step, Step (b). The formulator can remove the methanol as it is formed to drive the reaction to completion. In fact, the relative amount of alcohol by-product which is present can be used as a tool to control the extent of trans-sulfation. However, any alcohol, $R^1OH$ which is formed during Step (b) can be removed by any process which is convenient to the formulator, for example, absorption into a molecular sieve (zeolite), crystallization, precipitation, etc. In many instances, removal of the by-product alcohol during the reaction will be preferred. A preferred method for removal is by volatilization.

The following are non-limiting examples of the process according to the present invention. In the examples below, B represents the balance of a molecule not comprising an alcohol or amine moiety and is not meant to restrict the type of hydroxyl-containing compound which can be sulfated according to the present invention.

EXAMPLE 1

The following depicts an amino alcohol to be sulfated wherein the amino moiety also serves as to form the sulfating species.

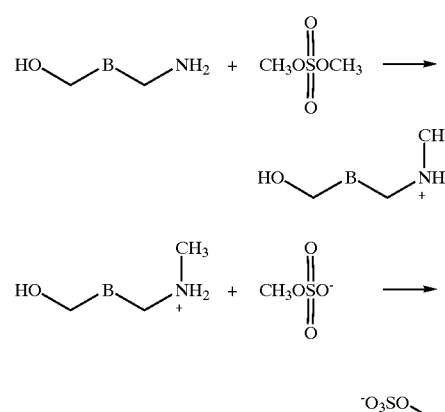

EXAMPLE 2

A molecule comprising two hydroxyl moieties is sulfated using a diamine in step (a).

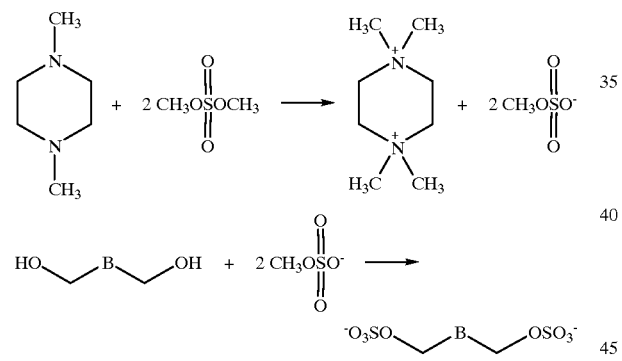

Utilizing the principle set forth in the present process that for each equivalent of hydroxyl unit to be sulfated an equivalent of sulfating species must be formed thereby requiring the consumption of an equivalent amount of an amine moiety, the process or the present invention can be expressed as a process comprising the steps of:

a) reacting n equivalents of an amine moiety with n equivalents of a sulfation precursor to form n equivalents of a sulfating species; and b) reacting said n equivalents of a sulfating species with a substrate having n equivalents of hydroxyl moieties to form a compound having n sulfated hydroxyl moieties.

Preferably the process of the present invention comprises the steps of:

a) reacting under non-acidic conditions n equivalents of a tertiary amine moiety with n equivalents of a sulfation precursor to form a sulfating species; and b) reacting under acidic conditions said sulfating species with a substrate having n hydroxyl moieties to form a compound having n sulfate moieties.

EXAMPLE 3

In another embodiment of the present invention, an amine-comprising, preferably a tertiary amine comprising compound having n amine moieties and m hydroxy moieties is sulfated according to the present process wherein an auxiliary amine having n' amine moieties is added in step (a) wherein the sum of n+n'=m.

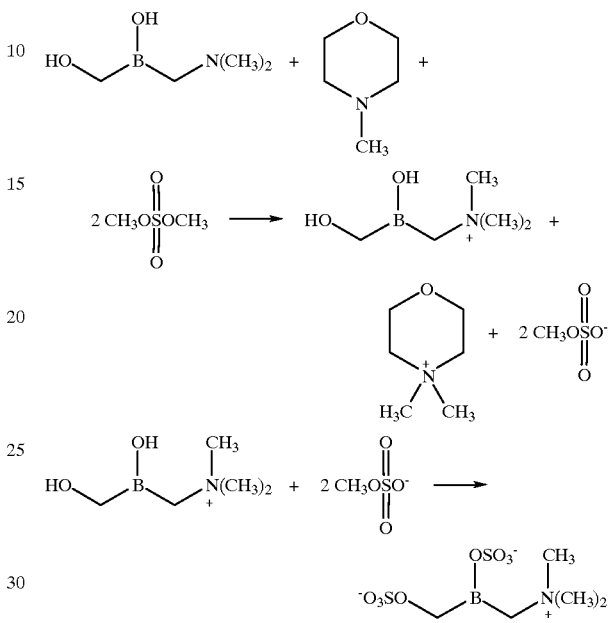

The process of the present invention can be used together with other sulfating species, for example, a compound comprising n amine moieties and m hydroxyl moieties wherein m>n, can have n hydroxyl moieties trans-sulfated by the process of the present invention without the addition of a second source of an amine, followed by subsequent sulfation of the balance of the hydroxyl moieties by another sulfation process.

EXAMPLE 4

In another embodiment of the present invention, a polyalkyleneoxy polyalkyleneimine having the general formula:

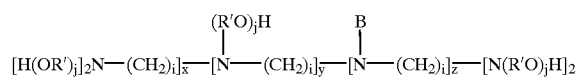

wherein $R^1$ is $C_2$–$C_4$ alkylene, B is a continuation by branching, i is from 1 to 12, j is from 1 to 50, x+y+z is from 3 to about 100; can be trans-sulfated to a species having the formula:

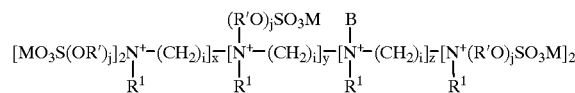

wherein the number of sulfated hydroxyl units is equal to the number of $R^1$ units transferred. The $R^1$ units which are transferred include the number which quaternize the polyalkyleneimine backbone as well as those which react with any auxiliary amine which is present.

EXAMPLE 5

Step (a): Quaternization of dimethyl ethanolamine (DMEA) EO20 to 90+mol % (1 mol N per mol polymer)—

To a 250 ml, 3-neck round bottom flask fitted with argon inlet, condenser, addition funnel, thermometer, mechanical stirring and argon outlet (connected to a bubbler) is charged dimethyl ethanol amine EO20 (27.5 g, 0.03 mol) and methylene chloride (20 g) under argon. The mixture is stirred at room temperature until the substrate has dissolved. The mixture is then cooled to 5° C. using an ice bath. Dimethyl sulfate (3.8 g, 0.03 mol, Aldrich, 99%, m.w.—126.13 ) is slowly added using an addition funnel over a period of 2 minutes. After all the dimethyl sulfate is added, the ice bath is removed and the reaction is allowed to rise to room temperature. After 24–48 hrs. the reaction is completed.

Step (b): Trans-sulfation of methyl sulfate salt of 90+% quaternized dimethyl ethanolamine EO20 1 mol N per mol polymer)—To the above apparatus is added a Dean Stark trap and condenser. Under argon, the reaction mixture from Step (a) is heated to 60° C. for 30 minutes to distill off volatile materials. Sufficient sulfuric acid (0.2 g) is added in order to achieve a pH approximately 2 (pH measured by taking an aliquot taken from reaction, dissolved up to 10% in water. Vacuum is applied to the reaction (25 mbar) and is allowed to stir for 60 minutes at 80° C. while collecting any volatile liquids. Once reaction is complete, the clear, light yellow liquid is neutralized to pH greater than 7 with 1N NaOH.

What is claimed is:

1. A trans-sulfation process comprising the steps of:
   a) reacting a tertiary amine with a sulfation precursor having the formula:

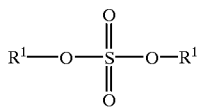

wherein $R^1$ is $C_1$–$C_{22}$ alkyl, $C_7$–$C_{22}$ alkylenearyl, and mixtures thereof; to form an admixture comprising a quaternized amine and a sulfating species; and
   b) reacting a hydroxyl species with said admixture to form a sulfated hydroxyl species.

2. A process according to claim 1 wherein $R^1$ is selected from the group consisting of methyl, ethyl, propyl, butyl, benzyl, and mixtures thereof.

3. A process according to claim 2 wherein said alkyl sulfate is dimethyl sulfate.

4. A process according to claim 1 wherein said tertiary amine comprises n amine moieties and m hydroxyl moieties wherein m>n.

5. A process according to claim 4 wherein said amine once sulfated in step (b) is further reacted with one or more other sulfating species.

6. A process according to claim 1 wherein step (a) is conducted at a first temperature and step (b) is conducted at a second temperature.

7. A process according to claim 1 wherein step (a) is conducted at a temperature of from about 0° C. to about 200° C. and step (b) is conducted at a temperature of from about 0° C. to about 200° C.

8. A process according to claim 1 wherein step (a) is conducted under neutral or basic conditions.

9. A process according to claim 1 wherein step (b) is conducted under acidic conditions.

10. A process according to claim 1 wherein step (a) is conducted in the presence of a solvent.

11. A process according to claim 1 wherein step (b) is conducted in the presence of a solvent.

12. A process according to claim 1 further comprising the step of isolating said sulfated hydroxyl species.

13. A process according to claim 1 wherein said process further comprises the step of removing the by-product alcohol which is formed in Step (b).

14. A process according to claim 1 wherein said hydroxyl species comprises one or more tertiary amine moieties which function as the tertiary amine in Step (a).

15. A trans-sulfation process comprising the steps of:
   a) reacting a hydroxyl species which further comprises a tertiary amine with a sulfation precursor having the formula:

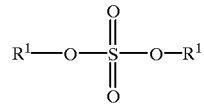

wherein $R^1$ is $C_1$–$C_{22}$ alkyl, $C_7$–$C_{22}$ alkylenearyl, and mixtures thereof; to form an admixture comprising a hydroxyl species which comprises a quaternized amine and a sulfating species; and
   b) further reacting said admixture until forming a sulfated hydroxyl species also comprising a quaternized tertiary amine.

16. A process according to claim 15 wherein said process further comprises the step of removing the by-product alcohol which is formed in Step (b).

17. A trans-sulfation process comprising the steps of:
   a) reacting a hydroxyl species which further comprises at least one amine moiety with a sulfation precursor having the formula:

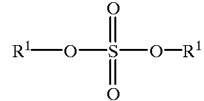

wherein $R^1$ is $C_1$–$C_{22}$ alkyl, $C_7$–$C_{22}$ alkylenearyl, and mixtures thereof; to form an admixture comprising a hydroxyl species which comprises at least one amine which has been alkylated by a —$R^1$ unit and a sulfating species; and
   b) further reacting said admixture until forming a sulfated hydroxyl species which also comprises an alkylated amine.

18. A process according to claim 17 wherein said process further comprises the step of removing the by-product alcohol which is formed in Step (b).

19. A sulfation process comprising the steps of:
   a) reacting n equivalents of an amine moiety with n equivalents of a sulfation precursor to form n equivalents of a sulfating species; and
   b) reacting said n equivalents of a sulfating species with a substrate having m equivalents of hydroxyl moieties to form a compound having up to n sulfated hydroxyl moieties.

20. A process according to claim 19 wherein said process further comprises the step of removing the by-product alcohol which is formed in Step (b).

21. A process according to claim 19 wherein said hydroxyl species comprises one or more tertiary amine moieties which function as the tertiary amine in Step (a).

22. A process according to claim 19 wherein said sulfation precursor is dimethylsulfate.

23. A process according to claim 19 wherein said process is conducted in the presence of a solvent.

24. A process according to claim 19 wherein step (a) is conducted at a temperature of from about 0° C. to about 200° C. and step (b) is conducted at a temperature of from about 0° C. to about 200° C.

25. A sulfation process comprising the steps of:
   a) reacting n equivalents of a tertiary amine moiety with n equivalents of a sulfation precursor to form n equivalents of a sulfating species; and
   b) reacting said n equivalents of a sulfating species with a substrate having m equivalents of hydroxyl moieties to form a compound having up to n sulfated hydroxyl moieties.

26. A process according to claim 25 wherein said sulfation precursor is dimethyl sulfate.

27. A process according to claim 25 wherein said process is conducted in the presence of a solvent.

28. A process according to claim 25 wherein step (a) is conducted at a temperature of from about 0° C. to about 200° C. and step (b) is conducted at a temperature of from about 0° C. to about 200° C.

29. A sulfation process comprising the steps of:
   a) reacting an amine-comprising compound having n equivalents of amine moieties and an auxiliary amine having n' equivalents of amine moieties with n+n' equivalents of a sulfation precursor to form n+n' equivalents of sulfating species, and wherein said amine-comprising compound further comprises m hydroxyl moieties; and
   b) forming m or less sulfated hydroxyl moieties.

30. A process according to claim 29 wherein said sulfation precursor is dimethyl sulfate.

31. A process according to claim 29 wherein said process is conducted in the presence of a solvent.

32. A process according to claim 29 wherein step (a) is conducted at a temperature of from about 0° C. to about 200° C. and step (b) is conducted at a temperature of from about 0° C. to about 200° C.

33. A sulfation process comprising the steps of:
   a) reacting under non-acidic conditions a compound comprising one or more amine moieties with one or more sulfation precursors to form an admixture of a compound having at least one alkylated amine moiety and a sulfating species; and
   b) reacting said admixture with one or more compounds comprising one or more hydroxyl moieties to form one or more sulfate compounds wherein at least one hydroxy unit is sulfated.

34. A process according to claim 33 wherein said process further comprises the step of removing the by-product alcohol which is formed in Step (b).

* * * * *